(12) United States Patent
Buck et al.

(10) Patent No.: US 8,132,101 B2
(45) Date of Patent: Mar. 6, 2012

(54) METHOD AND SYSTEM FOR DATA SELECTION AND DISPLAY

(75) Inventors: Schuyler Buck, Muncie, IN (US); Jason Bush, Fishers, IN (US); Wendy Yee, Ellicott City, MD (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 881 days.

(21) Appl. No.: 11/999,896

(22) Filed: Dec. 7, 2007

(65) Prior Publication Data

US 2009/0150440 A1 Jun. 11, 2009

(51) Int. Cl.
*G06F 3/00* (2006.01)
*G06F 3/01* (2006.01)
(52) U.S. Cl. ........ 715/708; 715/810; 715/825; 715/835; 715/844
(58) Field of Classification Search .................. 715/503, 715/708, 810, 825, 835, 844
See application file for complete search history.

(56) References Cited

U.S. PATENT DOCUMENTS

| | | | |
|---|---|---|---|
| 5,251,126 A * | 10/1993 | Kahn et al. ..................... | 600/309 |
| 5,307,455 A | 4/1994 | Higgins et al. | |
| 5,546,516 A | 8/1996 | Austel et al. | |
| 5,671,409 A | 9/1997 | Fatseas et al. | |
| 5,877,775 A | 3/1999 | Theisen et al. | |
| 6,024,699 A | 2/2000 | Surwit et al. | |
| 6,032,119 A | 2/2000 | Brown et al. | |
| 6,322,502 B1 | 11/2001 | Schoenberg et al. | |
| 6,356,256 B1 | 3/2002 | Leftwich | |
| 6,425,863 B1 | 7/2002 | Werner et al. | |
| 6,562,001 B2 | 5/2003 | Lebel et al. | |
| 6,564,105 B2 | 5/2003 | Starkweather et al. | |
| 6,571,128 B2 | 5/2003 | Lebel et al. | |
| 6,577,899 B2 | 6/2003 | Lebel et al. | |
| 6,585,644 B2 | 7/2003 | Lebel et al. | |
| 6,605,038 B1 | 8/2003 | Teller et al. | |
| 6,635,014 B2 | 10/2003 | Starkweather et al. | |
| 6,648,821 B2 | 11/2003 | Lebel et al. | |
| 6,659,948 B2 | 12/2003 | Lebel et al. | |
| 6,667,743 B2 | 12/2003 | Bertram et al. | |
| 6,668,196 B2 | 12/2003 | Villegas et al. | |
| 6,687,546 B2 | 2/2004 | Lebel et al. | |
| 6,694,191 B2 | 2/2004 | Starkweather et al. | |
| 6,733,446 B2 | 5/2004 | Lebel et al. | |
| 6,740,075 B2 | 5/2004 | Lebel et al. | |

(Continued)

FOREIGN PATENT DOCUMENTS

EP 0 970 655 A1 1/2000

(Continued)

OTHER PUBLICATIONS

Shahar, Y. et al., "*Distributed, intelligent, interactive visualization and exploration of time-oriented clinical data and their abstractions*"; Artificial Intelligence in Medicine, 2006, pp. 115-135, vol. 38.

(Continued)

*Primary Examiner* — Nicholas Augustine
(74) *Attorney, Agent, or Firm* — Faegre Baker & Daniels

(57) ABSTRACT

A method and apparatus for concurrently displaying sets of data related to a medical condition, including a feature which enables the user to select one or more of the data sets for emphasized or more prominent display relative to the other data set(s).

20 Claims, 4 Drawing Sheets

U.S. PATENT DOCUMENTS

| | | | |
|---|---|---|---|
| 6,748,402 | B1 | 6/2004 | Reeves et al. |
| 6,758,810 | B2 | 7/2004 | Lebel et al. |
| 6,781,522 | B2 | 8/2004 | Sleva et al. |
| 6,804,656 | B1 | 10/2004 | Rosenfeld et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,813,519 | B2 | 11/2004 | Lebel et al. |
| 6,852,104 | B2 | 2/2005 | Blomquist |
| 6,873,268 | B2 | 3/2005 | Lebel et al. |
| 6,958,705 | B2 | 10/2005 | Lebel et al. |
| 7,020,508 | B2 | 3/2006 | Stivoric et al. |
| 7,023,440 | B1 | 4/2006 | Havekost et al. |
| 7,024,236 | B2 | 4/2006 | Ford et al. |
| 7,029,455 | B2 | 4/2006 | Flaherty |
| 7,038,680 | B2 | 5/2006 | Pitkow |
| 7,039,703 | B1 | 5/2006 | Clancy et al. |
| 7,041,468 | B2 | 5/2006 | Drucker et al. |
| 7,050,735 | B2 | 5/2006 | Bardolatzy et al. |
| 7,063,665 | B2 | 6/2006 | Hasegawa et al. |
| 7,071,940 | B2 | 7/2006 | Malik |
| 7,072,356 | B1 | 7/2006 | Clancy et al. |
| 7,079,140 | B2 | 7/2006 | Boehler et al. |
| 7,082,334 | B2 | 7/2006 | Boute et al. |
| 7,165,062 | B2 | 1/2007 | O'Rourke |
| 7,179,226 | B2 | 2/2007 | Crothall et al. |
| 7,207,009 | B1 | 4/2007 | Aamodt et al. |
| 7,647,237 | B2 * | 1/2010 | Malave et al. ............. 705/3 |
| 2002/0016568 | A1 | 2/2002 | Lebel et al. |
| 2002/0029776 | A1 | 3/2002 | Blomquist |
| 2002/0040208 | A1 | 4/2002 | Flaherty et al. |
| 2002/0140976 | A1 | 10/2002 | Borg et al. |
| 2002/0193679 | A1 | 12/2002 | Malave et al. |
| 2003/0011646 | A1 | 1/2003 | Levine et al. |
| 2003/0065308 | A1 | 4/2003 | Lebel et al. |
| 2003/0065536 | A1 | 4/2003 | Hansen et al. |
| 2003/0098869 | A1 | 5/2003 | Arnold et al. |
| 2003/0145206 | A1 | 7/2003 | Wolosewicz et al. |
| 2003/0163088 | A1 | 8/2003 | Blomquist |
| 2003/0199739 | A1 | 10/2003 | Gordon et al. |
| 2003/0208110 | A1 | 11/2003 | Maultet et al. |
| 2003/0208465 | A1 | 11/2003 | Yurko |
| 2003/0233257 | A1 | 12/2003 | Matian et al. |
| 2004/0073464 | A1 | 4/2004 | Huang |
| 2004/0119742 | A1 | 6/2004 | Silbey et al. |
| 2004/0172284 | A1 | 9/2004 | Sullivan et al. |
| 2005/0004947 | A1 | 1/2005 | Emlet et al. |
| 2005/0137653 | A1 | 6/2005 | Friedman et al. |
| 2005/0159977 | A1 | 7/2005 | Green et al. |
| 2005/0192844 | A1 | 9/2005 | Esler et al. |
| 2006/0010014 | A1 | 1/2006 | Brown |
| 2006/0010098 | A1 * | 1/2006 | Goodnow et al. ............. 707/1 |
| 2006/0020491 | A1 | 1/2006 | Mongeon et al. |
| 2006/0031094 | A1 | 2/2006 | Cohen et al. |
| 2006/0265249 | A1 * | 11/2006 | Follis et al. ............. 705/3 |
| 2006/0272652 | A1 | 12/2006 | Stocker et al. |
| 2007/0033074 | A1 | 2/2007 | Nitzan et al. |
| 2007/0048691 | A1 | 3/2007 | Brown |
| 2007/0055940 | A1 | 3/2007 | Moore et al. |
| 2007/0089071 | A1 | 4/2007 | Zinn et al. |
| 2007/0179352 | A1 | 8/2007 | Randlov et al. |
| 2007/0185390 | A1 | 8/2007 | Perkins et al. |
| 2007/0189590 | A1 | 8/2007 | Fidrich et al. |
| 2007/0232866 | A1 | 10/2007 | Nephin et al. |
| 2007/0276197 | A1 | 11/2007 | Harmon |
| 2008/0244453 | A1 * | 10/2008 | Cafer ............. 715/835 |
| 2010/0057043 | A1 * | 3/2010 | Kovatchev et al. ............. 604/504 |

FOREIGN PATENT DOCUMENTS

| | | | |
|---|---|---|---|
| EP | 0 649 316 B1 | | 12/2000 |
| EP | 1 179 769 | | 2/2002 |
| EP | 1 194 864 A2 | | 4/2002 |
| EP | 1 416 417 | | 5/2004 |
| EP | 1 647 929 | | 4/2006 |
| EP | 1 839 615 | | 10/2007 |
| JP | 2004145774 A | | 5/2004 |
| JP | 2004145775 A | | 5/2004 |
| JP | 2004145776 A | | 5/2004 |
| JP | 2007058685 A | | 3/2007 |
| WO | WO 99/35856 | | 7/1999 |
| WO | WO0018449 | | 4/2000 |
| WO | WO 00/65522 | | 11/2000 |
| WO | WO0072181 | | 11/2000 |
| WO | WO0200111 | | 1/2002 |
| WO | WO02078512 | | 10/2002 |
| WO | WO03015838 | | 2/2003 |
| WO | WO2005037095 | | 4/2005 |
| WO | WO2005096206 | | 10/2005 |
| WO | WO2006050485 | | 2/2006 |
| WO | WO2007093482 | | 8/2007 |
| WO | WO 2008/147567 | | 12/2008 |

OTHER PUBLICATIONS

"CoPilot Health Management System Version 3.1," User's Guide, Mar. 2007, 230 pp., ART 10641 Rev. D, Abbott Diabetes Care, Inc.

"MediSense® Precision Link® Diabetes Data Management Software," User's Guide, May 2006, 58 pp., 116-412 Rev. AC, Abbott Diabetes Care, Inc.

Albisser, Michael A.; "A Graphical User Interface for Diabetes Management Than Integrates Glucose Prediction and Decision Support," Diabetes Technology & Therapeutics, 2005, pp. 264-273, vol. 7, No. 2.

Janssen et al., "Acensia® Winglucofacts® Professional Intelligent Diabetes Management Software Is an Effective Tool for the Management of Diabetes," Bayer HealthCare Clinical Summary Report, Jul. 2005, 10 pp.

Joshy et al.; "Diabetes Information Systems: A Rapidly Emerging Support for Diabetes Surveillance and Care," Diabetes Technology & Therapeutics, 2006, pp. 587-597, vol. 8, No. 5.

"OneTouch Diabetes Management Software," User Manual, 2006, 173 pp., v. 2.3.1, LifeScan, Inc.

"Getting Started, CareLink Personal Therapy Management Software for Diabetes," Brochure, 2007, 20 pp., Medtronic MiniMed, Inc.

"Accu-Chek® Camit Pro Diabetes Management Software," User's Manual, 2005, 220 pp., v.2.1 and Addendum v. 2.4, Roche Diagnostics Corp.

"Accu-Chek® Compass Diabetes Care Software," User's Guide, 2005, 74 pp., Roche Diagnostics Corp.

"Accu-Chek® Diabetes Assistant," accessed with notional data and printed from www.diabetesassistant.com on Jan. 16, 2007, 20 pp., Roche Diagnostics Corp.

Hotchkiss et al., "MD-Adapt: A Proposed Architecture for Open-Source Medical Device Interoperabiity", High Confidence Medical Devices, Software, and Systems and Medical Device Plug-and-Play Interoperability, 2007, Joint Workshop on IEEE, Jun. 2007.

Cabri et al., "Agent-Based Plug-and-Play Integration of Role-Enabled Medical Devices", High Confidence Medical Devices, Software, and Systems and Medical Device Plug-and-Play Interoperability, 2007, Joint Workshop on IEEE, Jun. 2007.

Wang et al., "A Corba-Based Object Frame-Work With Patient Identification Translation and Dynamic Linking. Methods for Exchanging Patient Data", Methods of Information in Medicine, vol. 38, No. 1, Mar. 1999.

Bilenko et al., "Adaptive Name Matching in Information Integration", IEEE Intelligent Systems, vol. 18, No. 5, Sep. 2003.

HAVi Specification, "The HAVi Specification: Specification of the Home Audio / Video Interoperability (HAVi) Architecture", Nov. 1998.

International Search Report and Written Opinion of the International Searching Authority, PCT/EP2008/009857, Mar. 6, 2009.

International Search Report and Written Opinion of the International Searching Authority, PCT/EP2008/009874, Mar. 13, 2009.

International Search Report and Written Opinion of the International Searching Authority, PCT/EP2008/009876, Apr. 6, 2009.

International Search Report and Written Opinion of the International Searching Authority, PCT/EP2008/009879, Mar. 9, 2009.

* cited by examiner

METHOD AND SYSTEM FOR DATA SELECTION AND DISPLAY

FIELD OF THE INVENTION

The present invention generally relates to graphical tools for healthcare monitoring systems, and more particularly to graphical tools for emphasizing a selected data set from among a plurality of data sets presented on a display.

BACKGROUND OF THE INVENTION

A variety of different medical treatments require monitoring of certain physiological parameters indicative of a patient's medical condition. Typically, the patient and/or a healthcare provider studies the monitored parameters and makes changes to the treatment as indicated by the analysis of the monitored parameters. As a general rule, the healthcare provider's ability to optimize the patient's treatment improves with increases in the amount of high quality data available for analysis. Larger quantities of data, however, become increasingly difficult to analyze and interpret, especially when relationships between different physiological parameters must be discerned to fully understand the patient's condition.

The treatment of diabetes, for example, involves a detailed analysis of a relatively large amount of data collected over a period of time. In addition to blood glucose (bG) measurements, the data may include information and measurements of A1c values, Albumin values, Albumin excretion values, body mass index values, blood pressure values, carbohydrate values, cholesterol values (total, HDL, LDL, ratio) creatinine values, fructosamine values, HbA1 values, height values, insulin dose values, insulin rate values, total daily insulin values, ketone values, microalbumin values, proteinuria values, heart rate values, temperature values, triglyceride values, and weight values, exercise, sleep, stress, etc. When considered together, relationships and trends between these various parameters emerge, and provide valuable insight to the healthcare provider for making adjustments to the patient's treatment regimen. It is, however, difficult to discern these relationships and trends by simply reviewing the raw data in, for example, tabular format.

SUMMARY OF THE INVENTION

The present invention provides a method and apparatus for displaying multiple sets of data related to a medical condition. In general, the invention provides a graphical representation of the multiple data sets such that two or more sets of data are presented on the same chart or graph. By default, one of the sets of data is more prominently displayed that the other set(s) of data. In this manner, the healthcare provider analyzing the data may simultaneously view data representing multiple physiological parameters to better understand the relationships between the data sets.

The invention further provides a "focus" feature which enables the user to select one of the multiple data sets and obtain a graphical display of the data sets wherein the selected data set is more prominently displayed relative to the other data sets. In one embodiment of the invention, the unselected data sets are de-emphasized relative to their normal display status. Using the focus feature, the user may toggle through each of the multiple sets of simultaneously displayed data and more clearly view the selected data set against the backdrop of the unselected data sets. In this manner, the user can more easily concentrate on a selected data set, yet still view the unselected data sets to identify relationships among the data sets.

The features of the present invention described above, as well as additional features, will be readily apparent to those skilled in the art upon reference to the following description and the accompanying drawings.

DETAILED DESCRIPTION OF EMBODIMENTS OF THE INVENTION

Figure 1:
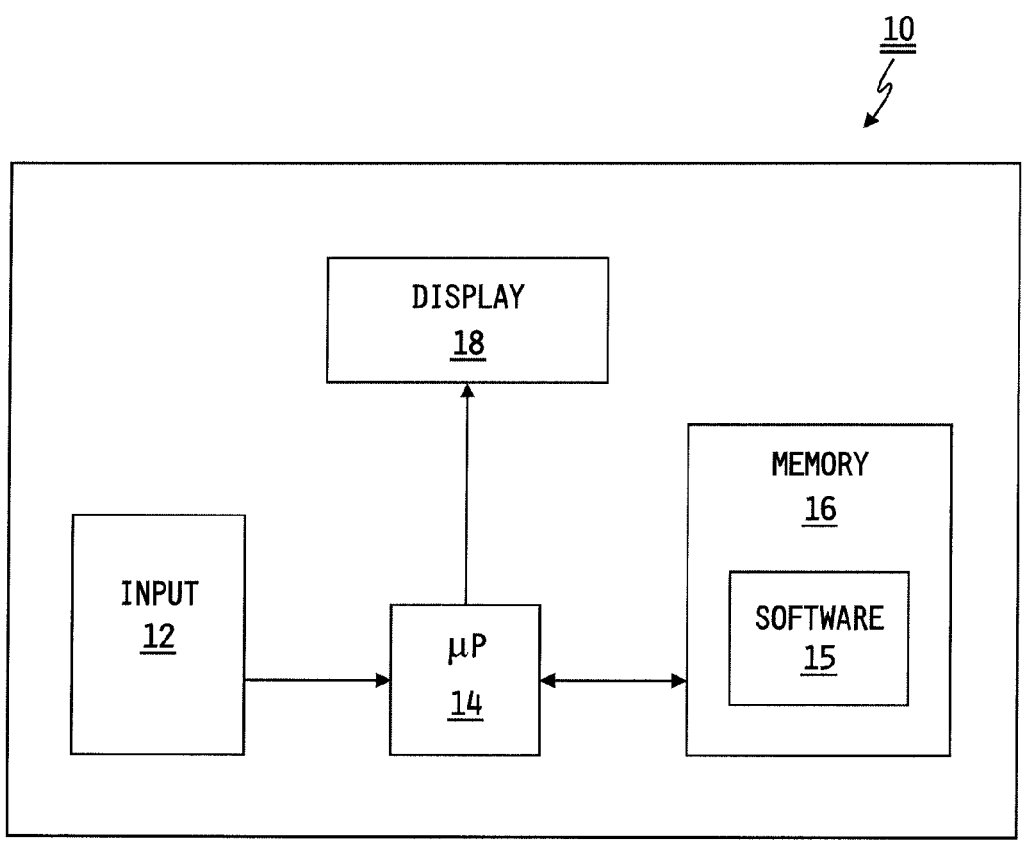
FIG. 1 is a conceptual diagram of components of a system according to the present invention.

The embodiments described below are merely exemplary and are not intended to limit the invention to the precise forms disclosed. Instead, the embodiments were selected for description to enable one of ordinary skill in the art to practice the invention.

It should be understood from the beginning that the subject matter of the present invention may readily be adapted to a variety of different applications. In general, where it is desirable to view more than one data set concurrently (i.e., overlaid graphically, perhaps having at least one common axis), the present invention may be utilized. Examples of such applications include data analysis in scientific pursuits, medical applications, social sciences, information technology, and business applications, to name a few. Each of these areas involve the act of analyzing multiple data sets with the aim of extracting information which may facilitate reaching conclusions about the underlying subject matter. Thus, each of these fields of endeavor may benefit from features of the present invention.

Concepts described below may be further explained in one of more of the co-filed patent applications entitled HELP UTILITY FUNCTIONALITY AND ARCHITECTURE Ser. No. 11/999,906, METHOD AND SYSTEM FOR GRAPHICALLY INDICATING MULTIPLE DATA VALUES Ser. No. 11/999,853, SYSTEM AND METHOD FOR DATABASE INTEGRITY CHECKING Ser. No. 11/999,856, METHOD AND SYSTEM FOR DATA SOURCE AND MODIFICATION TRACKING Ser. No. 11/999,888, PATIENT-CENTRIC HEALTHCARE INFORMATION MAINTENANCE Ser. No. 11/999,874, EXPORT FILE FORMAT WITH MANIFEST FOR ENHANCED DATA TRANSFER Ser. No. 11/999,867, GRAPHIC ZOOM FUNCTIONALITY FOR A CUSTOM REPORT Ser. No. 11/999,932, METHOD AND SYSTEM FOR SELECTIVE MERGING OF PATIENT DATA Ser. No. 11/999,859, METHOD AND SYSTEM FOR PERSONAL MEDICAL DATA DATABASE MERGING Ser. No. 11/999,772, METHOD AND SYSTEM FOR WIRELESS DEVICE COMMUNICATION Ser. No. 11/999,879, METHOD AND SYSTEM FOR SETTING TIME BLOCKS Ser. No. 11/999,968, METHOD AND SYSTEM FOR ENHANCED DATA TRANSFER Ser. No. 11/999,911, COMMON EXTENSIBLE DATA EXCHANGE FORMAT Ser. No. 11/999,871, METHOD OF CLONING SERVER INSTALLATION TO A NETWORK CLIENT Ser. No. 11/999,876, METHOD AND SYSTEM FOR QUERYING A DATABASE Ser. No. 11/999, 912, METHOD AND SYSTEM FOR EVENT BASED DATA COMPARISON Ser. No. 11/999,921, DYNAMIC COMMUNICATION STACK Ser. No. 11/999,934, SYSTEM AND METHOD FOR REPORTING MEDICAL INFORMATION Ser. No. 11/999,878, METHOD AND SYSTEM FOR MERGING EXTENSIBLE DATA INTO A DATABASE USING GLOBALLY UNIQUE IDENTIFIERS Ser. No. 11/999,947, METHOD AND SYSTEM FOR ACTIVATING FEATURES AND FUNCTIONS OF A CONSOLIDATED SOFTWARE APPLICATION Ser. No. 11/999,880, METHOD AND SYSTEM FOR CONFIGURING A CONSOLIDATED SOFTWARE APPLICATION Ser. No. 11/999, 894, METHOD AND SYSTEM FOR ASSOCIATING DATABASE CONTENT FOR SECURITY ENHANCEMENT Ser. No. 11/999,951, METHOD AND SYSTEM FOR CREATING REPORTS Ser. No. 11/999,851, METHOD AND SYSTEM FOR CREATING USER-DEFINED OUTPUTS Ser. No. 11/999,905, DATA DRIVEN COMMUNICATION PROTOCOL GRAMMAR Ser. No. 11/999,770, HEALTHCARE MANAGEMENT SYSTEM HAVING IMPROVED PRINTING OF DISPLAY SCREEN INFORMATION Ser. No. 11/999,855, and METHOD AND SYSTEM FOR MULTI-DEVICE COMMUNICATION Ser. No. 11/999,866, the entire disclosures of which are hereby expressly incorporated herein by reference. It should be understood that the concepts described below may relate to diabetes management software systems for tracking and analyzing health data, such as, for example, the Accu-Chek® 360° product provided by Roche Diagnostics. As indicated above, however, the concepts described herein may also have applicability to apparatuses, methods, systems, and software in fields that are unrelated to healthcare. Furthermore, it should be understood that references in this patent application to devices, meters, monitors, pumps, or related terms are intended to encompass any currently existing or later developed apparatus that includes some or all of the features attributed to the referred to apparatus, including but not limited to the Accu-Chek® Active, Accu-Chek® Aviva, Accu-Chek® Compact, Accu-Chek® Compact Plus, Accu-Chek® Integra, Accu-Chek® Go, Accu-Chek® Performa, Accu-Chek® Spirit, Accu-Chek® D-Tron Plus, and Accu-Chek® Voicemate Plus, all provided by Roche Diagnostics or divisions thereof.

Also, reference is made in the following description to storage of data in a database. The actual physical implementation of a database on a general purpose computer may take several forms, from complete individual records storing the substantive information with several key indexes for locating a particular record, to a plurality of tables interrelated by relational operations, to a matrix of cross-linked data records, to various combinations and hybrids of these general types. In particular physical devices, a database may be structured and arranged to accommodate the restrictions of the physical device but, when transferred to a general purpose computer, be able to be stored in a variety of formats. Thus, while certain types of information may be described as being stored in a "database" from a conceptual standpoint, generally such information may be electronically stored in a variety of structures with a variety of encoding techniques.

Although the following description details operations in terms of a graphic user interface using display objects, the present invention may be practiced with text based interfaces, or even with voice or visually activated interfaces.

Before delving into the various embodiments of the system and method according to the invention, general healthcare management system concepts will be described. A general healthcare management system receives medical data from a plurality of sources and displays the data to facilitate diagnosis and treatment of patients. Medical data is stored in fields within records in a database. Each record may contain a plurality of data fields. Data originating in devices external to the computing device, whether originated in a laboratory, a medical device, or generated manually in another computing device, must be transferred into the computing device before it may be managed by the system. Data transfer mechanisms include downloading and merging. Downloading occurs when a device transmits data to the system. Specifically, downloading occurs when a medical device is accessible to the system and transfers data directly to the system. Downloading also occurs when data is first transferred to computer storage media before it is transferred from the computer storage media to the system. Merging, on the other hand, occurs when a computing device selectively transfers data from a source database, whether resident on the device or remote from it, to the system, or destination, database.

Referring now to FIG. 1, a system 10 according to one embodiment of the present invention includes a data input component 12, a processor 14 that executes a machine-readable program or software 15 including encoded instructions and stored in memory 16, and a display 18. Depending upon the implementation of system 10, data input component 12 may include a input device such as a standard or custom keypad or keyboard, a touch pad, a pointing device such as a mouse, a touch-sensitive screen or display (possibly incorporated into display 18), a joystick, speech recognition equipment, or any other interface device suitable for inputting data into system 10. Alternatively, data input component 12 may include a wired or wireless communication port for receiving data using any of a variety of analog or digital technologies such as infrared, radio frequency, telephony, Bluetooth, etc.

Processor 14 may include any of a variety of different digital electronic components configured to interpret program instructions and process data. Typically, processor 14 may include a semi-conducting integrated circuit which functions as a central processing unit for a larger set of electronics that provide functionality to system 10. Among its various functions depending upon the specific application, processor 14 is configured to provide commands and data to electronics associated with display 18 to cause data to be presented to a user on display 18 in the manner described in further detail below.

Display 18 may employ any of a variety of different display technologies such as vacuum fluorescent, electroluminescent, plasma, liquid crystal, light emitting diode, and any other technology suitable for presenting information to a user in graphical form. As will be understood by persons of ordinary skill in the art, display 18 includes a variety of electronic devices in addition to the visual output device viewed by the user which are necessary to enable the visual output device to perform its function.

System 10 may be a stand-alone system or part of a network of other devices. For example, system 10 may be an integrated part of or attachment to a handheld device such as a PDA, a bG meter, a cellular telephone, or other device. Alternatively, system 10 may be a conventional computing device in the form of a palm top, notebook, laptop or desk top computer. In any of the above forms, system 10 may be connected via wired or wireless technology to other systems and/or devices, or even distributed in terms of its functionality across a network of devices. For example, the data for display by system 10 may be stored and served using a remote serving device coupled to a network such as the Internet. In such an embodiment, at least part of the functionality of processor 14 is performed by the remote server, and input device 12 for system 10 may be coupled to a device that is entirely separate from the device including display 18.

Figure 2:
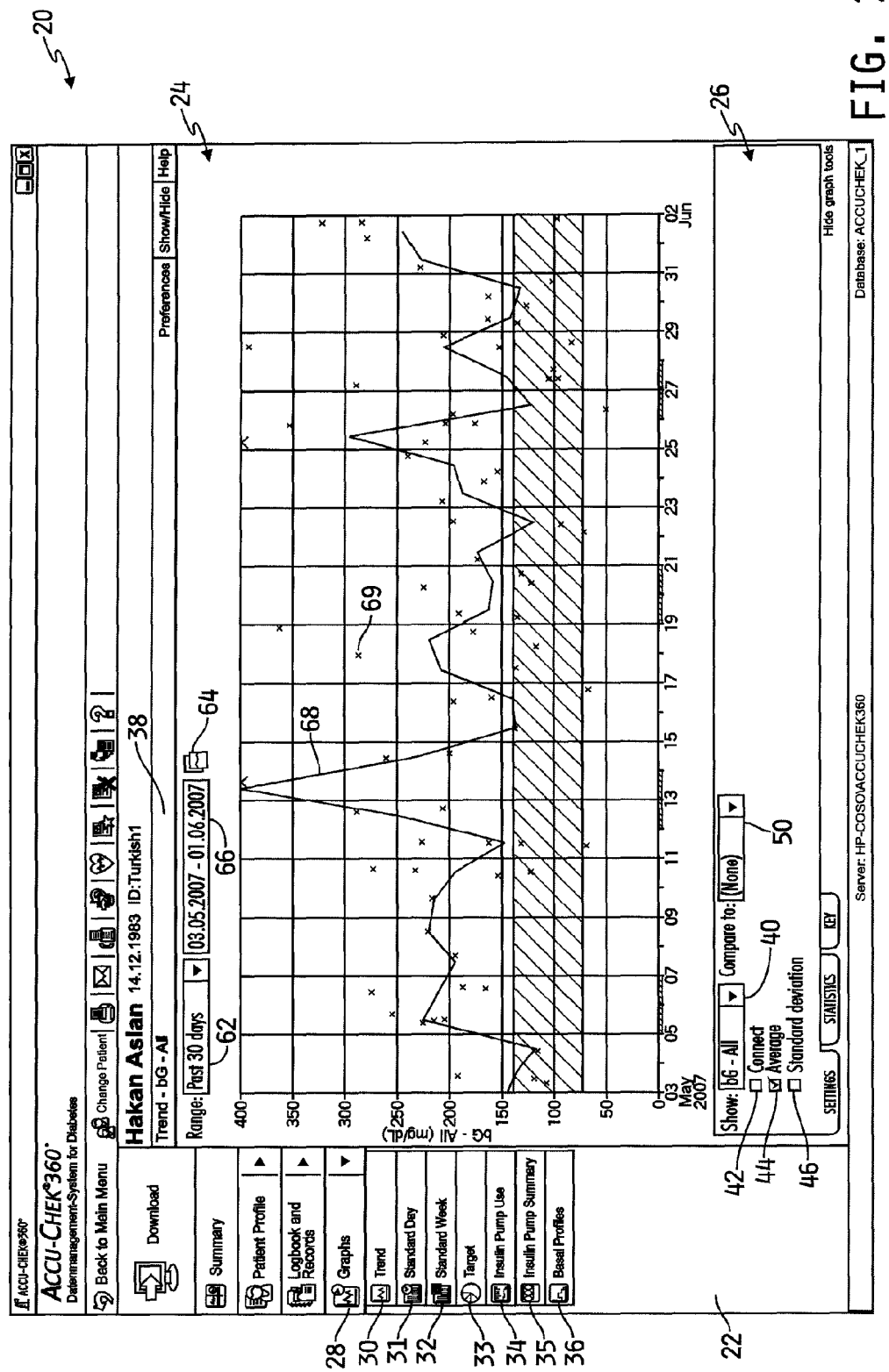
FIG. 2 is a screenshot generated by the system of FIG. 1 including a graphical display of a data set.

Referring now to FIG. 2, a screenshot 20 is shown on display 18. In this example, system 10 is employed to assist in the data analysis associated with the monitoring and treatment of a patient with diabetes. As shown, screenshot 20 includes a navigation area 22 for selecting various functions of the underlying software used to generate screenshot 20, a graph area 24, and a data settings area 26. One option in navigation area 22 is a graphs function button 28 (shown selected), which upon selection generates a list of graph options including trend 30, standard day 31, standard week 32, target 33, insulin pump use 34, insulin pump summary 35, and basal profiles 36. In FIG. 2, trend option 30 is selected as indicated by title bar 38. Software 15 responds to selection of graph function button 28 and trend option 30 by generating graph area 24. In one embodiment, graph area 24 is initially blank, and remains blank until the user selects options in data settings area 26 as described below. In an alternative embodiment, graph area 24 initially displays data selected during the last use of graph area 24. In yet another embodiment, graph area 24 initially displays a default selection of data sets. It should be noted that in one embodiment of the invention, when graph area 24 displays two or more data sets, one of the data sets is, by default, emphasized or more prominently displayed relative to the other data set(s).

Data settings area 26 includes a data select dropdown menu 40, which when selected by the user permits selection of any of a variety of different data sets stored in memory 16 of system 10. It should be understood that the data sets available for selection using dropdown menu 40 may include some or all of the data sets maintained in memory 16 for a selected patient. The data sets maintained in memory 16 may be predefined by software 15 or defined by a user. Data selection options 42, 44, 46 are also presented depending upon the selection of data select dropdown menu 40. Finally, data settings area 26 also includes a secondary data select dropdown menu 50, which is shown in FIG. 2 as having not been activated (i.e., no secondary data set has been selected).

Graph area 24 also includes a time period select dropdown menu 62, which when selected by the user permits selection from a list of predefined time periods such as, for example, the past 30 days, the past 2 days, all data corresponding to the selected patient, or a custom defined date range. A portion of the data sets selected in the manner described above corresponding to the selected time period will be displayed in graph area 24. As an alternative to the predefined time period options provided by time period select dropdown menu 62, graph area 24 further includes a calendar time select icon 64, which when selected presents the user with a calendar from which the user may select start and stop dates for the selected data sets. The selected start and stop dates are then displayed to the user in date box 66.

Data select dropdown menu 40 may provide data set options of bG data, insulin, carbs, weight data, exercise, etc. In screenshot 20, bG data has been selected. As shown, bG data is presented in units of milligram per deciliter along the y-axis of the plot in graph area 24. The x-axis corresponds to the time period selected using time period select dropdown menu 62. As the data selection option 44 is selected, the average bG data is provided as line 68. The individual bG measurements are shown as "X" icons numbered 69.

Figure 3:
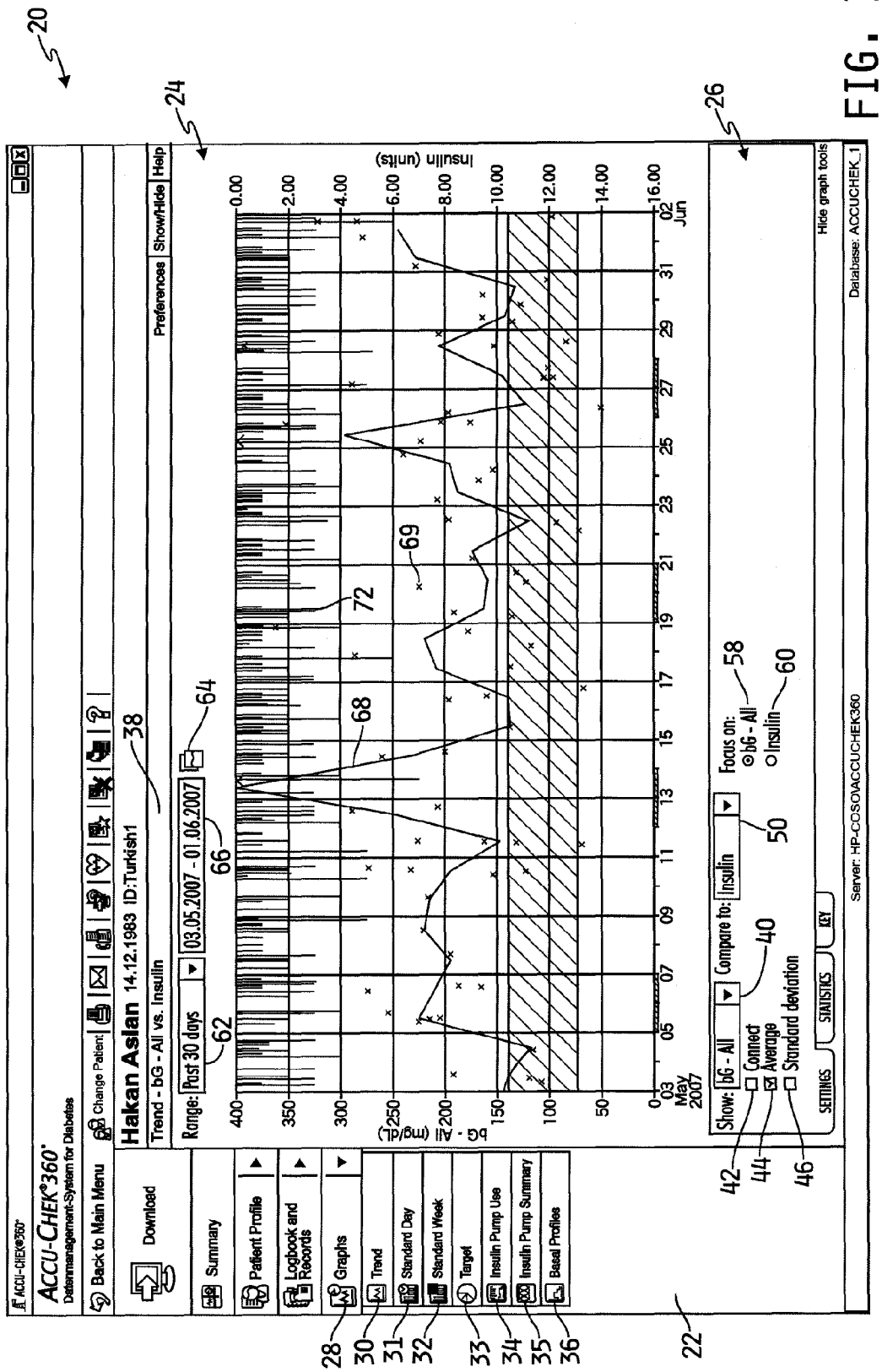
FIGS. 3 and 4 are screenshots similar to that of FIG. 2 including a graphical display of two data sets, one of which is displayed more prominently than the other.

FIG. 3 shows screenshot 20 after secondary data select dropdown menu 50 of data settings area 26 has been activated to select insulin as a data set for comparison to the previously selected bG data set. Depending upon the type of data set selected, when secondary data select dropdown menu 50 is activated, corresponding data selection options (like options 42, 44, 46) are presented to the user. For example, had the user selected weight data from menu 50, the user could specify that the weight data be presented as average weight and as individual weight measurements. In FIG. 3, insulin measurements 72 are shown along the top of the graph in accordance with the y-axis on the right hand side of graph area 24.

Additionally, when a secondary data set is selected for comparison, focus selection buttons 58, 60 are provided in data settings area 26. As should be apparent from the foregoing, focus selection buttons 58, 60 correspond to the data sets selected using data select dropdown menus 40, 50, respectively. In one embodiment of the invention, one of focus selection buttons 58, 60 is activated by default. When focus selection button 58 is selected as shown in FIG. 3 (i.e., the user has selected the bG data set as the prominent data set), lines 72 and the corresponding y-axis for insulin is de-emphasized, but still presented to the user. It should be understood that the prominent data set corresponding to bG data (and the corresponding y-axis) may also be emphasized relative to how it appears when no secondary data set had been selected (i.e., its "normal appearance") such as is shown in FIG. 2. In other words, not only may the non-selected data set be de-emphasized, the selected data set may be emphasized relative to its normal appearance. In yet another alternative embodiment, the prominent data set is emphasized relative to its normal appearance and the non-selected data set retains its normal appearance. In summary, the non-selected data set may be de-emphasized, the prominent data set may be emphasized, or the non-selected data set may be de-emphasized in addition to the prominent data set being emphasized.

Figure 4:
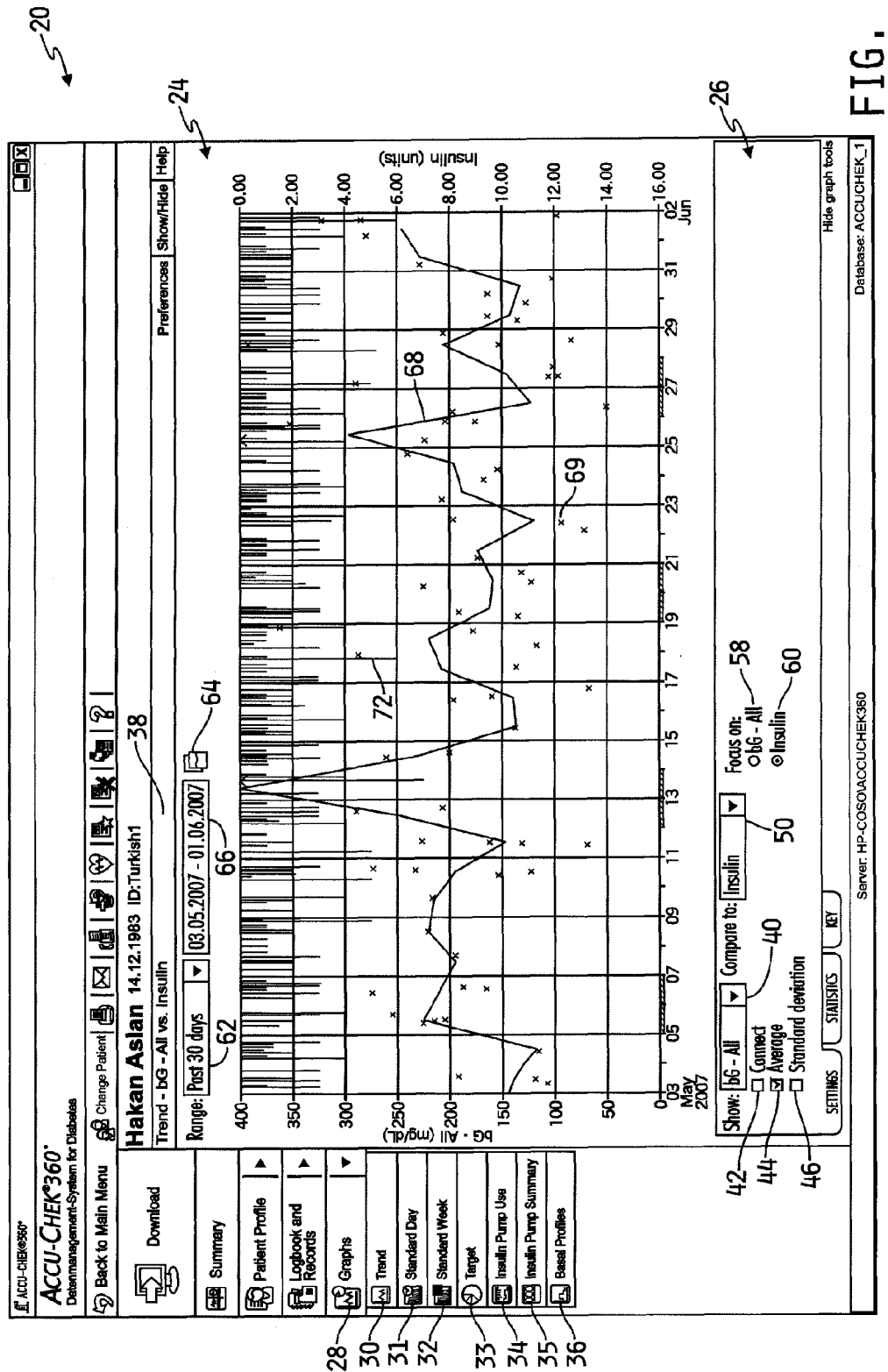

By simply clicking on focus selection buttons 58, 60, the user may toggle the display emphasis between the displayed data sets to more easily evaluate the relationships between the data sets. In FIG. 4, the insulin data set is emphasized. Although only two data sets are depicted in the figures, it should be understood that three or more data sets may be simultaneously displayed in graph area 24 in accordance with the present invention. In such embodiments, additional data select dropdown menus 40, 50 would be provided in data settings area 26. Additional focus selection buttons 58, 60 would also be provided to permit the user to change emphasis among the various data sets by selecting one data set to emphasize or multiple data sets to emphasize.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of displaying data, including the steps of:
   enabling a user to select a first data set;
   displaying the first data set within a region of a graph on a display, the graph including a first y-axis disposed at a first position of the graph and associated with the first data set, the first y-axis comprising a plurality of coordinates indicating a first unit of measure;
   enabling the user to select a second data set;
   displaying the second data set within the region of the graph on the display, the graph including a second y-axis associated with the second data set, the second y-axis disposed at a second position of the graph and comprising a plurality of coordinates indicating a second unit of measure distinct from the first unit of measure, the second position being distinct from the first position, the step of displaying the second data set performed concurrently with the step of displaying the first data set;

enabling the user to select one of the first data set and the second data set as a prominent data set; and responding to the user selection of the prominent data set by de-emphasizing the other of the first data set and the second data set not selected as the prominent data set, the first data set and the second data set remaining concurrently displayed within the region of the graph during the step of responding, wherein the region of the graph including the first y-axis overlaps with the region of the graph including the second y-axis.

2. The method of claim 1, further including the step of responding to the selection of the prominent data set by emphasizing the prominent data set.

3. The method of claim 1, wherein the first and the second data sets have a common x-axis.

4. The method of claim 1, further including the step of de-emphasizing the y-axis associated with the other of the first data set and the second data set not selected as the prominent data set.

5. The method of claim 1, wherein the step of enabling the user to select a first data set includes the step of displaying a dropdown menu of available data sets.

6. The method of claim 1, wherein the first data set relates to diabetes.

7. A system for displaying data, including:
a data input component configured to permit user selection of a first data set and a second data set;
a processor in communication with the data input component, the processor being configured to execute software instructions relating to the display of the first and second data sets; and
a display which, under control of the processor, generates a screen including a graph area that concurrently displays the selected first and second data sets within the graph area, the graph area including a first y-axis disposed at a first position and associated with the first data set, the first y-axis comprising a first plurality of coordinates representing a first unit of measure, the graph area also including a second y-axis disposed at a second position and associated with the second data set, the second y-axis comprising a second plurality of coordinates representing a second unit of measure distinct from the first unit of measure, the graph area including the first y-axis overlapping with the graph area including the second y-axis and the second position being distinct from the first position,
wherein the screen further includes a data settings area having options selectable using the data input component corresponding to the selected first and second data sets, the processor responding to selection of a first option by causing the display to change the prominence of one of the first and second data sets relative to the other of the first and second data sets while concurrently displaying the first and second data sets within the graph area.

8. The system of claim 7, wherein the change in prominence of one of the first and second data sets comprises one of the first and second data sets being emphasized relative to the other of the first and second data set.

9. The system of claim 7, wherein the change in prominence of one of the first and second data sets comprises the other of the first and second data sets being de-emphasized relative to the other of the first and second data set.

10. The system of claim 7, wherein the options are radio buttons and the data input component is a pointing device.

11. The system of claim 7, wherein the graph area includes an x-axis that corresponds to both of the first and second data sets.

12. The system of claim 7, wherein the processor responds to selection of the first option by changing the prominence of the first y-axis relative to the second y-axis.

13. The system of claim 7, further including a memory configured to store the software instructions and the first and second data sets.

14. A method of displaying data performed by the execution of a plurality of encoded instructions on a machine readable program by a computing device, the method including the steps of
enabling a user to select at least two data sets;
concurrently displaying the data sets graphically within a graph area on a display, the graph area including a first y-axis associated with a first data set and disposed at a first location, and a second y-axis associated with a second data set and disposed at a second location distinct from the first location, the graph area including the first y-axis overlapping with the graph area including the second y-axis, the first y-axis comprising a plurality of coordinates representing a first unit of measure and the second y-axis comprising a plurality of coordinates representing a second unit of measure distinct from the first unit of measure;
enabling the user to select one of the data sets as a prominent data set; and
changing the prominence of the prominent data set relative to at least one other data set, the step of changing performed while concurrently displaying the data sets graphically on the display.

15. The method of claim 14, wherein the changing step includes the step of increasing the prominence of the prominent data set relative to the at least one other data set.

16. The method of claim 14, wherein the changing step includes the step of de-emphasizing the at least one other data set.

17. The method of claim 14, wherein a single x-axis is associated with the at least two data sets.

18. The method of claim 14, wherein the step of enabling the user to select one of the data sets as a prominent data set includes the step of displaying a user-selectable option for each of the at least two data sets.

19. The method of claim 15, wherein one of the at least two data sets includes blood glucose data.

20. The system of claim 7, wherein first unit of measure comprises a blood glucose value and the second unit of measure comprises an insulin value.

* * * * *